United States Patent [19]

Shawver et al.

[11] Patent Number: 5,512,358

[45] Date of Patent: Apr. 30, 1996

[54] MULTI-COMPONENT POLYMERIC STRANDS INCLUDING A BUTENE POLYMER AND NONWOVEN FABRIC AND ARTICLES MADE THEREWITH

[75] Inventors: Susan E. Shawver, Roswell; David C. Strack, Canton; Terry K. Timmons, Marietta; Debra J. McDowall, Roswell, all of Ga.

[73] Assignee: Kimberly-Clark Corporation, Neenah, Wis.

[21] Appl. No.: 125,624

[22] Filed: Sep. 22, 1993

[51] Int. Cl.$^6$ .............................. B32B 27/00; D02G 3/00; D04H 1/04

[52] U.S. Cl. .................... 428/286; 428/298; 428/302; 428/373; 428/374; 428/296

[58] Field of Search .................................. 428/373, 374, 428/284, 286, 288, 296, 298, 302

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,423,266 | 1/1969 | Davies et al. | 156/167 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,595,245 | 7/1971 | Buntin et al. | 131/269 |
| 3,595,731 | 7/1971 | Davies et al. | 161/150 |
| 3,676,242 | 7/1972 | Prentice | 156/62.4 |
| 3,692,618 | 9/1972 | Dorschner et al. | 161/72 |
| 3,704,198 | 11/1972 | Prentice | 161/148 |
| 3,715,251 | 2/1973 | Prentice | 156/62.8 |
| 3,802,817 | 4/1974 | Matsuki et al. | 425/66 |
| 3,855,046 | 12/1974 | Hansen et al. | 161/150 |
| 3,909,009 | 9/1975 | Cvetko et al. | 274/37 |
| 4,041,203 | 9/1977 | Brock et al. | 428/157 |
| 4,068,036 | 1/1978 | Stanistreet | 428/296 |
| 4,189,338 | 2/1980 | Ejima et al. | 156/167 |
| 4,340,563 | 7/1982 | Appel et al. | 264/518 |
| 4,451,589 | 5/1984 | Morman et al. | 523/124 |
| 4,477,516 | 10/1984 | Sugihara et al. | 428/296 |
| 4,523,336 | 6/1985 | Truman | 2/69 |
| 4,729,371 | 3/1988 | Krueger et al. | 428/374 |
| 4,797,318 | 1/1989 | Brooker et al. | 428/288 |
| 5,057,361 | 10/1991 | Sayovitz et al. | 428/290 |
| 5,108,820 | 4/1992 | Kaneko et al. | 428/198 |
| 5,108,827 | 4/1992 | Gessner | 428/219 |
| 5,165,979 | 11/1992 | Watkins et al. | 428/113 |
| 5,204,174 | 4/1993 | DaPonte et al. | 428/286 |
| 5,208,098 | 5/1993 | Stover | 428/284 |
| 5,336,552 | 8/1994 | Strack et al. | 428/224 |

FOREIGN PATENT DOCUMENTS

| | | |
|---|---|---|
| 803714 | 1/1969 | Canada . |
| 0337662 | 10/1989 | European Pat. Off. . |
| 0456044 | 11/1991 | European Pat. Off. .......... D04H 1/42 |
| 0482918 | 4/1992 | European Pat. Off. .......... B32B 5/26 |
| 0586924A1 | 3/1994 | European Pat. Off. . |
| 1-246413 | 10/1989 | Japan . |
| 1112358 | 5/1968 | United Kingdom .............. D01F 7/00 |
| 1134924 | 11/1968 | United Kingdom .............. D01F 7/02 |
| 1217892 | 12/1970 | United Kingdom . |
| 93/06168 | 4/1993 | WIPO . |

OTHER PUBLICATIONS

John A. Manson & Leslie H. Sperling—"Polymer Blends & Composites" pp. 273–277. Published 1976, 77, & 81 by a Division of Plenum Publishing Corporation, 227 West 17th Street, New York, N.Y. 10010.

Hoechst Celanese—"Dictionary of Fiber & Textile Technology" pp. 14–15 & 32–33. Published 1990 by Hoechst Celanese Corporation P.O. Box 32414, Charlotte, North Carolina 28232.

Database WPI. Section Ch, Week 8945, Derwent Publications Ltd., London, GB; Class A, AN 89–329611 & JP A,126,413 (Idemitsu Petrochem KK) 2 Oct. 1989. See Abstract.

Wente, V. A., "Superfine Thermoplastic Fibers," Industrial and Engineering Chemistry, vol. 48, No. 8, pp. 1342–1346 (1956).

Primary Examiner—James D. Withers
Attorney, Agent, or Firm—James B. Robinson; William D. Herrick

[57] ABSTRACT

Multicomponent polymeric strands including a polymer blend of a butene polymer, a polyolefin other than butene, and up to 10% by weight of ethylene in polymeric form. The blend is in one side or the sheath of the multi-component strands. Fabric made with such strands is also disclosed and has enhanced softness properties. Composite materials including the foregoing fabric bonded to both sides of an inner meltblown layer and garments and other articles made with the fabric are also disclosed.

28 Claims, 5 Drawing Sheets

MULTI-COMPONENT POLYMERIC STRANDS INCLUDING A BUTENE POLYMER AND NONWOVEN FABRIC AND ARTICLES MADE THEREWITH

TECHNICAL FIELD

This invention generally relates to polymeric fibers and filaments and products such as nonwoven fabrics made with polymeric fibers and filaments. More particularly, this invention relates to multi-component polymeric fibers and filaments which include butene polymer compositions, and nonwoven fabrics and garments made with such fibers and filaments.

BACKGROUND OF THE INVENTION

Polymeric fibers and filaments are used to make a variety of products including yarns, carpets, woven fabrics, and nonwoven fabrics. As used herein, polymeric fibers and filaments are referred to generically as polymeric strands. Filaments mean continuous strands of material and fibers mean cut or discontinuous strands having a definite length.

It is often desirable that polymeric strands and articles made with polymeric strands be soft and strong. This is particularly true for nonwoven fabric and articles made with nonwoven fabric. Nonwoven fabrics are useful for a wide variety of applications, including garments, coverings, wraps, absorbent personal care products, medical applications, and cleaning applications. Nonwoven garments include protective workwear and medical apparel such as surgical gowns. Nonwoven personal care products include infant care items such as diapers, child care items such as training pants, feminine care items such as sanitary napkins, and adult care items such as incontinence products. Other nonwoven medical applications include nonwoven wound dressings and surgical dressings. Cleaning applications for nonwovens include towels and wipes. Still other uses of nonwoven fabrics are well known. The foregoing list is not considered exhaustive.

Nonwoven fabrics are commonly made by meltspinning thermoplastic materials. Meltspun fabrics are called spunbond materials and methods for making spunbond materials are well-known. U.S. Pat. No. 3,692,618 to Dorschner et al. and U.S. Pat. No. 4,340,563 to Appel et al. both disclose methods for making spunbond nonwoven webs from thermoplastic materials by extruding the thermoplastic material through a spinneret and drawing the extruded material into filaments with a stream of high velocity air to form a random web on a collecting surface. For example, U.S. Pat. No. 3,692,618 to Dorschner et al. discloses a process wherein bundles of polymeric filaments are drawn with a plurality of eductive guns by very high speed air. U.S. Pat. No. 4,340,563 to Appel et al. discloses a process wherein thermoplastic filaments are drawn through a single wide nozzle by a stream of high velocity air. The following patents also disclose typical meltspinning processes: U.S. Pat. No. 3,338,992 to Kinney; U.S. Pat. No. 3,341,394 to Kinney; U.S. Pat. No. 3,502,538 to Levy; U.S. Pat. No. 3,502,763 to Hartmann; U.S. Pat. No. 3,909,009 to Hartmann; U.S. Pat. No. 3,542,615 to Dobo et al.; and Canadian Patent Number 803,714 to Harmon.

Spunbond materials with desirable combinations of physical properties, especially combinations of strength, durability, and softness have been produced, but limitations have been encountered. For example, in some applications, polymeric materials such as polypropylene may have a desirable level of strength but not a desirable level of softness. On the other hand, materials such as polyethylene may, in some cases, have a desirable level of softness but a not a desirable level of strength.

In an effort to produce nonwoven materials having desirable combinations of physical properties, nonwoven fabrics comprising multi-component strands such as bicomponent strands or multiconstituent strands such as biconstituent strands have been developed.

Methods for making bicomponent nonwoven materials are well-known and are disclosed in patents such as Reissue U.S. Pat. No. 30,955 of U.S. Pat. No. 4,068,036 to Stanistreet, U.S. Pat. No. 3,423,266 to Davies et al., and U.S. Pat. No. 3,595,731 to Davies et al. A bicomponent nonwoven fabric is made from polymeric fibers or filaments including first and second polymeric components which remain distinct. The first and second components of multi-component strands are arranged in substantially distinct zones across the cross-section of the strands and extend continuously along the length of the strands. Typically, one component exhibits different properties than the other so that the strands exhibit properties of the two components. For example, one component may be polypropylene which is relatively strong and the other component may be polyethylene which is relatively soft. The end result is a strong yet soft nonwoven fabric.

Multiconstituent strands are similar to multi-component strands except that one component does not extend continuously along the length of the strands. The noncontinuous component is typically present as a multitude of discrete polymer segments connected by the other polymeric component.

Although conventional bicomponent and biconstituent nonwoven fabrics have desirable levels of strength, durability, and softness, there is still a need for nonwoven materials which are made with polymeric strands and have particular combinations of strength, durability, and softness. Furthermore, there is a need for garments and other articles made with nonwoven materials having particular combinations of strength, durability, and softness.

SUMMARY OF THE INVENTION

Accordingly, an object of the present invention is to provide improved polymeric strands and products made therewith such as nonwovens and garments.

Another object of the present invention is to provide polymeric strands, nonwoven fabrics made with polymeric strands, and articles such as garments made with nonwoven fabrics, each having desirable levels of strength, durability, and softness.

A further object of the present invention is to provide soft yet strong and durable nonwoven articles such as garments and absorbent articles.

Thus, the present invention provides a multi-component polymeric strand wherein one of the components comprises a polymeric blend which includes a butene polymer. More particularly, the multi-component polymeric strand includes first and second polymeric components arranged in substantially distinct zones across the cross-section of a strand and extending continuously along the length of the strand. The first component constitutes at least a portion of the peripheral surface of the strand continuously along the length of the strand. The first polymeric component comprises a blend of a butene polymer, a first polyolefin other than a butene polymer, and up to 10% percent by weight of ethylene in polymer form. The addition of the butene polymer softens the strand and fabric made therewith without reducing the strength or abrasion resistance of the strand or fabric to undesirable levels. The amount of ethylene molecules in the polymers which form the first polymeric component blend is no more than about 10% by weight of the first polymeric component, and preferably no more than about 5.5% by weight of the first polymeric component, so that the strength and durability of the strand and the fabric made therewith is sufficiently high.

The butene polymer of the first polymeric component can be a butene homopolymer or a butene copolymer. Suitable butene copolymers comprise butene in an amount of at least 90% by weight of the butene copolymer. Preferably, the butene polymer is a homopolymer of butene-1 or a copolymer of butene-1 and another olefin. Suitable butene copolymers should have no more than about 10% by weight ethylene molecules and preferably comprise not more than about 5.5% by weight ethylene molecules.

Suitable first polyolefins for blending with the butene polymer in the first polymeric component include polypropylene and copolymers of propylene and ethylene with ethylene being present in an amount from about 1 to 10% by weight of the copolymer, and preferably being present in an amount from about 1 to about 3% by weight of the copolymer. The copolymer of propylene and ethylene is preferably a random copolymer.

Preferably, the butene polymer is present in the first polymeric component in an amount from about 2 to about 50% by weight of the first component and the first polyolefin is present in the first polymeric component in an amount from about 98 to 50% by weight of the first component. More particularly, the butene polymer is present in the first polymeric component in an amount from about 15 to about 25% by weight of the first component.

Suitable polymers for the second component include polyolefins. Polyolefins for the second component should include no more than about 10% by weight ethylene molecules. More particularly, suitable polyolefins for the second components include polypropylene and copolymers of propylene and ethylene with ethylene being present in an amount from about 1 to about 10% by weight of the copolymer, and preferably from about 1 to about 3% by weight of the copolymer. The copolymer of propylene and ethylene is preferably a random copolymer.

Suitable configurations for the first and second components of the multi-component strands include a side-by-side configuration and a sheath/core configuration. The strands can be discontinuous fibers or continuous filaments.

The present invention also comprehends a nonwoven fabric made with the above-described polymeric strands and further comprehends articles such as garments, cleaning articles, and absorbent personal care articles made with such nonwoven fabric. In addition, the present invention comprehends a composite nonwoven fabric wherein a first web of multi-component polymeric strands of the present invention is bonded to a second web of extruded polymeric strands. In a preferred embodiment, the composite fabric has three layers, the middle layer comprising meltblown strands of polymeric material and the outer layers comprising the above-described multi-component strands of the present invention. Preferably, these multi-component strands are spunbond. The addition of the butene polymer to the multi-component strands enhances the softness of the strands and the nonwoven fabric and articles made therewith while maintaining acceptable levels of durability and strength.

Still further objects and the broad scope of the applicability of the present invention will become apparent to those of skill in the art from the details given hereafter. However, it should be understood that the detailed description of the preferred embodiments of the present invention is only given by way of illustration because various changes and modifications well within the spirit and scope of the invention should become apparent to those of skill in the art in view of the following detailed description.

DETAILED DESCRIPTION OF THE INVENTION

Figure 1:
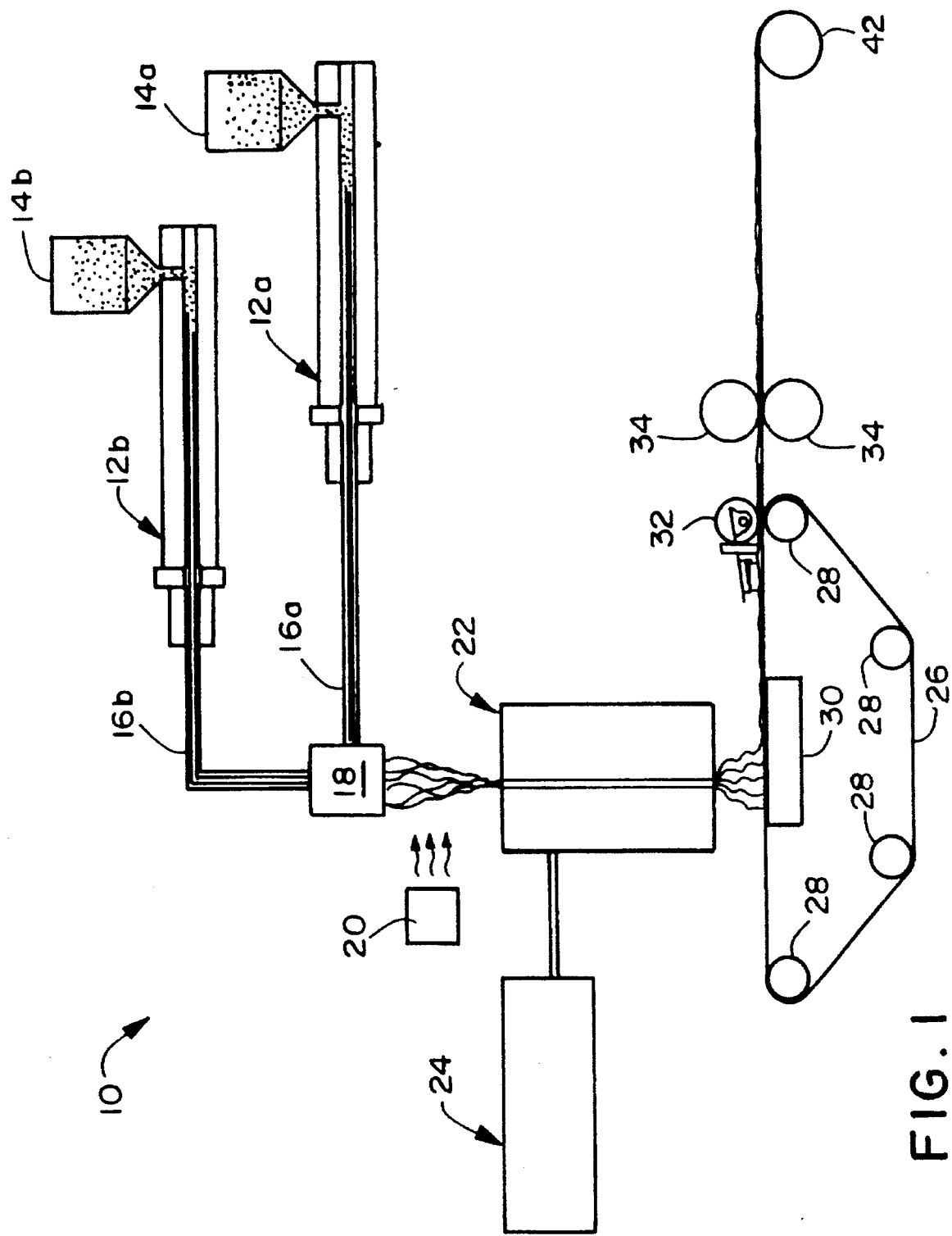
FIG. 1 is a schematic drawing of a process line for making a preferred embodiment of the present invention.

As discussed above, the present invention provides polymeric strands that are useful for making articles such as nonwoven fabrics. Nonwoven fabrics made with the polymeric strands of the present invention are soft, yet strong and durable. The nonwoven fabrics of the present invention can be used to make other useful articles.

The term "strands" as used herein refers to an elongated extrudate formed by passing a polymer through a forming orifice such as a die. Strands include fibers, which are discontinuous strands having a definite length, and filaments, which are continuous strands of material. The polymeric strands of the present invention are multi-component polymeric strands. Bicomponent polymeric strands are preferred, but it should be understood that the multi-component strands of the present invention can comprise more than two polymeric components.

Generally described, the multi-component polymeric strands of the present invention include first and second melt-extrudable polymeric components. The first and second components of the multi-component strands are arranged in substantially distinct zones across the cross-section of the multi-component strands and extend continuously along the length of the multi-component strands. The first component of the multi-component strands constitutes at least a portion of the peripheral surface of the strands continuously along the length of the strands.

As will be explained in more detail below, the first component of the multi-component strands comprises a blend of a butene polymer, a first polyolefin other than a butene polymer, and up to about 10% by weight of ethylene in polymeric form.

Nonwoven webs may be formed by a variety of processes such as meltblowing, spunbonding, film aperturing, and staple fiber carding. The nonwoven fabric of the present invention can be formed from staple multi-component fibers. Such staple fibers may be carded and bonded to form the nonwoven fabric. Preferably, however, the nonwoven fabric of the present invention is made with continuous spunbond multi-component filaments which are extruded, drawn, and laid on a traveling forming surface. A preferred process for making the nonwoven fabrics of the present invention is disclosed in detail below.

The nonwoven fabrics of the present invention can be used to make garments, coverings, sterilization wraps, absorbent personal care products, medical products, and cleaning products. Suitable garments include protective workwear and medical apparel such as surgical gowns. Suitable personal care products include infant care items such as diapers, child care items such as training pants, feminine care items such as sanitary napkins, and adult care items such as incontinence products. Other nonwoven medical products include nonwoven wound dressings and surgical gowns, drapes, and dressings. Cleaning products include towels and wipes. There are still other uses of the nonwoven fabrics of the present invention. The foregoing list is not considered exhaustive.

The butene polymer in the first component of the multi-component strand can be a butene homopolymer or a butene copolymer. The butene copolymer should contain at least 90% by weight of butene with the remainder being another olefin such as ethylene. Thus, the butene polymer comprises butene in an amount from about 90 to about 100% by weight of the butene polymer. Suitable butene polymers include homopolymer of butene-1 and copolymer of butene-1 and another olefin such as ethylene. A particularly suitable, commercially available butene polymer is the Duraflex® DP-8510 copolymer available from Shell Chemical Company of Houston, Tex.

Suitable polyolefins for combination with the butene polymer in the first component of the multi-component strand include polypropylene and copolymers of propylene and ethylene with ethylene being present in an amount from about 1 to about 10% by weight of the copolymer and preferably from about 1 to about 3% by weight of the copolymer. A particularly preferred, commercially available copolymer is PD-9355 random copolymer of propylene and ethylene available from Exxon Chemical Company of Houston, Tex.

Preferably, the butene polymer is present in the first component of the multi-component strand in an amount from about 2 to about 50% by weight of the first component and the first polyolefin is present in the first polymeric component in an amount from about 98 to 50% by weight of the first component. More particularly, the butene polymer is present in the first component in an amount from about 15 to about 25% by weight of the first component.

Suitable polymers for the second component of the multi-component strands include polyolefins. The polyolefin of the second component should include not more than about 10% by weight ethylene. More particularly, suitable second polyolefins for the second component include polypropylene and copolymers of propylene and ethylene with ethylene being present in an amount from about 1 to about 10% by weight of the copolymer and preferably from about 1 to about 3% by weight of the copolymer. A particularly suitable, commercially available polypropylene is PP-3445 polypropylene available from Exxon Chemical Company of Houston, Tex., and a particularly suitable, commercially available random copolymer is PD-9355 random copolymer of propylene and ethylene available from Exxon Chemical Company.

When the polymeric strand of the present invention is a multi-component strand, the strand is preferably in a bicomponent configuration with either a sheath/core arrangement or a side-by-side arrangement. The weight ratio of the first polymeric component to the second polymeric component may vary from 20/80 to 80/20, but preferably is about 50/50.

Figure 2A:
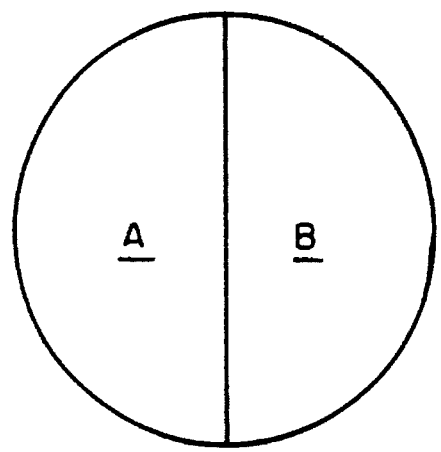
FIG. 2A is a schematic drawing illustrating the cross-section of a filament made according to a preferred embodiment of the present invention with the polymer components A and B in a side-by-side arrangement.
Figure 2B:
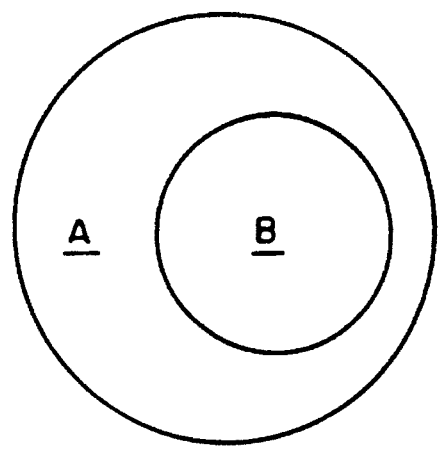
FIG. 2B is a schematic drawing illustrating the cross-section of a filament made according to a preferred embodiment of the present invention with the polymeric components A and B in an eccentric sheath/core arrangement.
Figure 2C:
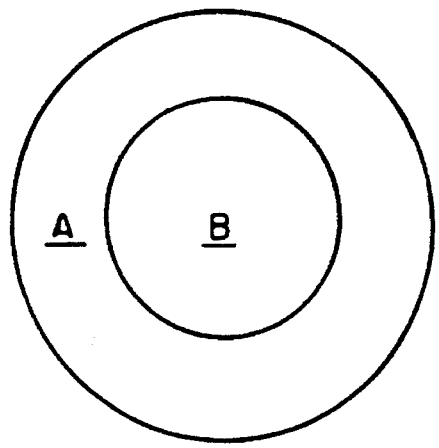
FIG. 2C is a schematic drawing illustrating the cross-section of a filament made according to a preferred embodiment of the present invention with the polymeric components A and B in a concentric sheath/core arrangement.

A preferred embodiment of the present invention is a bicomponent polymeric strand comprising a first polymeric component A and a second polymeric component B. The first and second components A and B may be arranged in a side-by-side arrangement as shown in FIG. 2A, and eccentric sheath/core arrangement as shown in FIG. 2B, or a concentric sheath/core arrangement as shown in FIG. 2C. Polymer component A is the sheath of the strand and polymer component B is the core of the strand in the sheath/core arrangement. When arranged in the side-by-side arrangement or the eccentric sheath/core arrangement, the resulting strands tend to exhibit natural helical crimp. Methods for extruding bicomponent polymeric strands into such arrangements are well known to those of ordinary skill in the art.

A preferred combination of polymers for the first component of the bicomponent strand of the present invention is a blend of a random copolymer of propylene and ethylene, having 3% by weight ethylene, and a butene copolymer comprising 94.5% by weight butene-1 and 5.5% by weight ethylene. The second component is preferably polypropylene. While the principal components of the polymeric strands of the present invention have been described above, such polymeric components can also include other materials which do not adversely affect the objectives of the present invention. For example, the first and second polymeric components A and B can also include, without limitation, pigments, anti-oxidants, stabilizers, surfactants, waxes, solid solvents, particulates and materials added to enhance processability of the composition.

Turning to FIG. 1, a process line 10 for preparing a preferred embodiment of the present invention is disclosed. The process line 10 is arranged to produce bicomponent continuous filaments, but it should be understood that the present invention comprehends nonwoven fabrics made with multi-component filaments having more than two components. For example, the fabric of the present invention can be made with filaments having three or four components.

The process line 10 includes a pair of extruders 12a and 12b for separately extruding a polymer component A and a polymer component B. Polymer component A is fed into the respective extruder 12a from a first hopper 14a and polymer component B is fed into the respective extruder 12b from a second hopper 14b. Polymer components A and B are fed from the extruders 12a and 12b through respective polymer conduits 16a and 16b to a spinneret 18. Spinnerets for extruding bicomponent filaments are well-known to those of ordinary skill in the art and thus are not described here in detail. Generally described, the spinneret 18 includes a housing containing a spin pack which includes a plurality of plates stacked one on top of the other with a pattern of openings arranged to create flow paths for directing polymer components A and B separately through the spinneret. The spinneret 18 has openings arranged in one or more rows. The spinneret openings form a downwardly extending curtain of filaments when the polymers are extruded through the spinneret. Preferably, spinneret 18 is arranged to form side-by-side or eccentric sheath/core bicomponent filaments. Such configurations are shown in FIG. 2A and 2B respectively. The spinneret may also be arranged to form concentric sheath/core filaments as shown in FIG. 2C.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1, or both sides of the filament curtain.

A fiber draw unit or aspirator 22 is positioned below the spinneret 18 and receives the quenched filaments. Fiber draw units or aspirators for use in melt spinning polymers are well-known as discussed above. For example, suitable fiber draw units for use in the process of the present invention include a linear fiber aspirator of the type shown in U.S. Pat. No. 3,802,817, eductive guns of the type shown in U.S. Pat. Nos. 3,692,618 and 3,423,266, and a linear draw system such as that shown in U.S. Pat. No. 4,340,563, the disclosures of which patents are hereby incorporated herein by reference.

Generally described, the fiber draw unit 22 includes an elongated vertical passage through which the filaments are drawn by aspirating air entering from the sides of the passage and flowing downwardly through the passage. The aspirating air draws the filaments and ambient air through the fiber draw unit. The aspirating air can be heated by a heater 24 when a high degree of natural helical crimp in the filaments is desired.

An endless foraminous forming surface 26 is positioned below the fiber draw unit 22 and receives the continuous filaments from the outlet opening of the fiber draw unit. The forming surface 26 travels around guide rollers 28. A vacuum box 30 positioned below the forming surface 26 where the filaments are deposited draws the filaments against the forming surface.

The process line 10 further includes a compression roller 32 which can be heated. The compression roller 32 and the forward-most of the guide rollers 28 receive the web as the web is drawn off of the forming surface 26. In addition, the process line includes a pair of thermal point bonding rollers 34 for bonding the bicomponent filaments together and integrating the web to form a finished fabric. Lastly, the process line 10 includes a winding roll 42 for taking up the finished fabric.

To operate the process line 10, the hopper 14a and 14b are filled with the respective polymer components A and B. Polymer components A and B are melted and extruded by the respected extruders 12a and 12b through polymer conduits 16a and 16b and the spinneret 18. Although the temperatures of the molten polymers vary depending on the polymers used, when component A comprises butene copolymer and random copolymer of ethylene and propylene and component B comprises polypropylene, the preferred temperatures of the polymers range from about 370° to about 530° F. and preferably range from 390° to about 450° F.

As the extruded filaments extend below the spinneret 18, a stream of air from the quench blower 20 at least partially quenches the filaments. The partial quenching may be used to develop a latent helical crimp in the filaments. The quench air preferably flows in a direction substantially perpendicular to the length of the filaments at a temperature of about 45° to about 90° F. and a velocity from about 100 to about 400 feet per minute.

After quenching, the filaments are drawn into the vertical passage of the fiber draw unit 22 by a flow of air through the fiber draw unit. The fiber draw unit is preferably positioned 30 to 60 inches below the bottom of the spinneret 18. When butene polymer is present in the filaments, the filaments tend to have natural helical crimp even when the aspirating air is at ambient temperature. However, when filaments having an increased degree of crimp are desired, heated air from the heater 24 is supplied to the fiber draw unit 22. For higher crimp, the temperature of the air supplied from the heater 24 is sufficient that, after some cooling due to mixing with cooler ambient air aspirated with the filaments, the air heats the filaments to a temperature required to activate the latent crimp. The temperature required to activate the latent crimp of the filaments ranges from about 110° F. to a maximum temperature less than the melting point of the second component B. The temperature of the air from the heater 24, and thus the temperature to which the filaments are heated, can be varied to achieve different levels of crimp. It should be further understood that the temperature of the air contacting the filaments to achieve the desired crimp will depend on factors such as the type of polymers in the filaments and the denier of the filaments.

Generally, a higher air temperature produces a higher number of crimps. The degree of crimp of the filaments may be controlled by controlling the temperature of the mixed air in the fiber draw unit 22 contacting the filaments. This allows one to change the resulting density, pore size distribution and drape of the fabric by simply adjusting the temperature of the air in the fiber draw unit.

Figure 3:
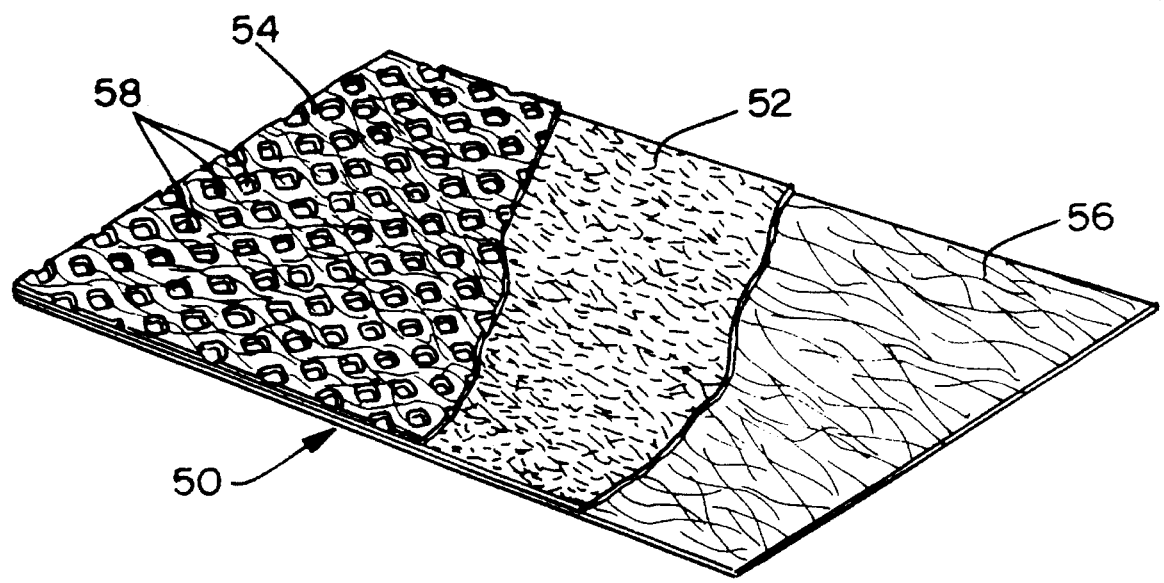
FIG. 3 is a fragmentary perspective view, with sections thereof broken away, of a point-bonded sample of multilayer fabric made according to a preferred embodiment of the present invention.
Figure 4:
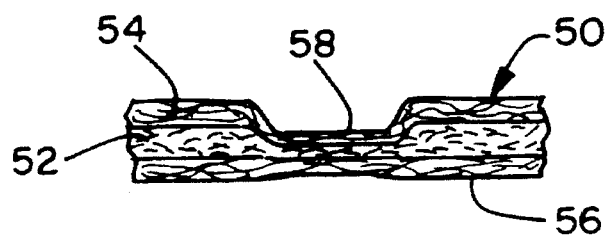
FIG. 4 is a cross-sectional view of the multilayer fabric of FIG. 3.

The drawn filaments are deposited through the outer opening of the fiber draw unit 22 onto the traveling forming surface 26. The vacuum 30 draws the filaments against the forming surface 26 to form an unbonded, nonwoven web of continuous filaments. The web is then lightly compressed by the compression roller 32 and thermal point bonded by bonding rollers 34. Thermal point bonding techniques are well known to those skilled in the art and are not discussed here in detail. Thermal point bonding in accordance with U.S. Pat. No. 3,855,046 is preferred and such reference is incorporated herein by reference. The type of bond pattern may vary based on the degree of strength desired. The bonding temperature also may vary depending on factors such as the polymers in the filaments but is preferably between about 240° and 290° F. As explained below, thermal point bonding is preferred when making cloth-like materials for garments such as medical apparel and workwear, and for making the outer cover of absorbent personal care items like baby diapers. A thermal point bonded material is shown in FIGS. 3 and 4. Lastly, the finished web is wound onto the winding roller 42 and is ready for further treatment or use.

When used to make liquid handling layers of liquid absorbent articles, the fabric of the present invention may be treated with conventional surface treatments or contain conventional polymer additives to enhance the wettability of the fabric. For example, the fabric of the present invention may be treated with polyalkalene-oxide modified siloxane such as polyalkaline-dioxide modified polydimethyl-siloxane as disclosed in U.S. Pat. No. 5,057,361. Such a surface treatment enhances the wettability of the fabric so that the nonwoven fabric is suitable as a liner or surge management material for feminine care, infant care, child care, and adult incontinence products. The fabric of the present invention may also be treated with other treatments such as antistatic agents, alcohol repellents, and the like, as known to those skilled in the art.

The resulting material is soft, yet durable and strong. The addition of the butene polymer tends to enhance the softness of the fabric while maintaining the strength and durability of the fabric at acceptable levels.

When used as a garment material, the nonwoven fabric of the present invention preferably has a denier from about 1 to about 12 dpf and more preferably has a denier from about 2 to about 3.5 dpf. The lower denier imparts improved cloth-like tactile properties to the fabric. The basis weight of such materials may vary but preferably ranges from about 0.4 to about 3.0 osy.

Although the method of bonding shown in FIG. 1 is thermal point bonding, it should be understood that the fabric of the present invention may be bonded by other means such as oven bonding, ultrasonic bonding, hydroentangling or combinations thereof to make cloth-like fabric. Such bonding techniques are well known to those of ordinary skill in the art and are not discussed here in detail. If a loftier material is desired, a fabric of the present invention may be bonded by non-compressive means such as through-air bonding. Methods of through-air bonding are well known to those of skill in the art. Generally described, the fabric of the present invention may be through-air bonded by forcing air having a temperature above the melting temperature of the first component A of the filaments through the fabric as the fabric passes over a perforated roller. The hot air melts the lower melting polymer component A and thereby forms bonds between the bicomponent filaments to integrate the web. Such a high loft material is useful as a fluid management layer of personal care absorbent articles such as liner or surge management material in a baby diaper.

According to another aspect of the present invention, the above described nonwoven fabric may be laminated to one or more polymeric layers to form a composite material. For example, an outer cover material may be formed by laminating the spunbond, nonwoven, thermal point bonded fabric described above to a polymeric film. The polymeric film can act as a liquid and particulate barrier and preferably comprises a polyolefin such as polypropylene and preferably has a thickness less than about 1 mil.

According to another embodiment of the present invention, a first web of extruded multi-component polymeric strands made as described above is bonded to a second web of extruded polymeric strands, the first and second webs being positioned in laminar surface-to-surface relationship. The second web may be a spunbond material, but for applications such as garment material for medical apparel or for sterile medical wrap, the second layer can be made by well known meltblowing techniques. The meltblown layer can act as a liquid barrier. Such laminates can be made in accordance with U.S. Pat. No. 4,041,203, the disclosure of which is incorporated herein by reference. U.S. Pat. No. 4,041,203 references the following publications on meltblowing techniques which are also incorporated herein by reference: An article entitled "Superfine Thermoplastic Fibers" appearing in INDUSTRIAL & ENGINEERING CHEMISTRY, Vol. 48, No. 8, pp. 1342–1346 which describes work done at the Naval Research Laboratories in Washington, D.C.; Naval Research Laboratory Report 111437, dated Apr. 15, 1954; U.S. Pat. Nos. 3,715,251; 3,704,198; 3,676,242; and 3,595,245; and British Specification No. 1,217,892.

The meltblown layer can comprise a blend of a butene polymer with another olefin. For example, the meltblown layer can comprise a blend of polypropylene or random copolymer of propylene and ethylene (preferably with 3% by weight ethylene) with 5–70% by weight butene polymer. As with the first component of the spunbond material, the butene polymer can be butene homopolymer or copolymer.

A third layer of nonwoven fabric comprising multi-component polymeric strands, as in the first web, can be bonded to the side of the second web opposite from the first web. When the second web is a meltblown layer, the meltblown layer is sandwiched between two layers of multi-component material. Such material 50 is illustrated in FIGS. 3 and 4 and is advantageous as a medical garment material because it can contain a liquid penetration resistant middle layer 52 with relatively soft layers of fabric 54 and 56 on each side for better softness and feel. The material 50 is preferably thermal point bonded. When thermal point bonded, the individual layers 52, 54, and 56 are fused together at bond points 58.

Such composite materials may be formed separately and then bonded together or may be formed in a continuous process wherein one web is formed on top of the other. Both of such processes are well known to those skilled in the art and are not discussed here in further detail. U.S. Pat. No. 4,041,203, which is incorporated herein by reference above, discloses both a continuous process and the use of preferred webs for making such composite materials.

Figure 5:
FIG. 5 is a perspective view of a medical garment made with nonwoven fabric according to a preferred embodiment of the present invention.

A medical garment 70 made according to an embodiment of the present invention is shown in FIG. 5. The construction of such garments of nonwoven fabric is well-known to those skilled the art and thus is not discussed here in detail. For example, a process for making medical garments is disclosed in U.S. Pat. No. 4,523,336, the disclosure of which is expressly incorporated herein by reference.

Figure 6:
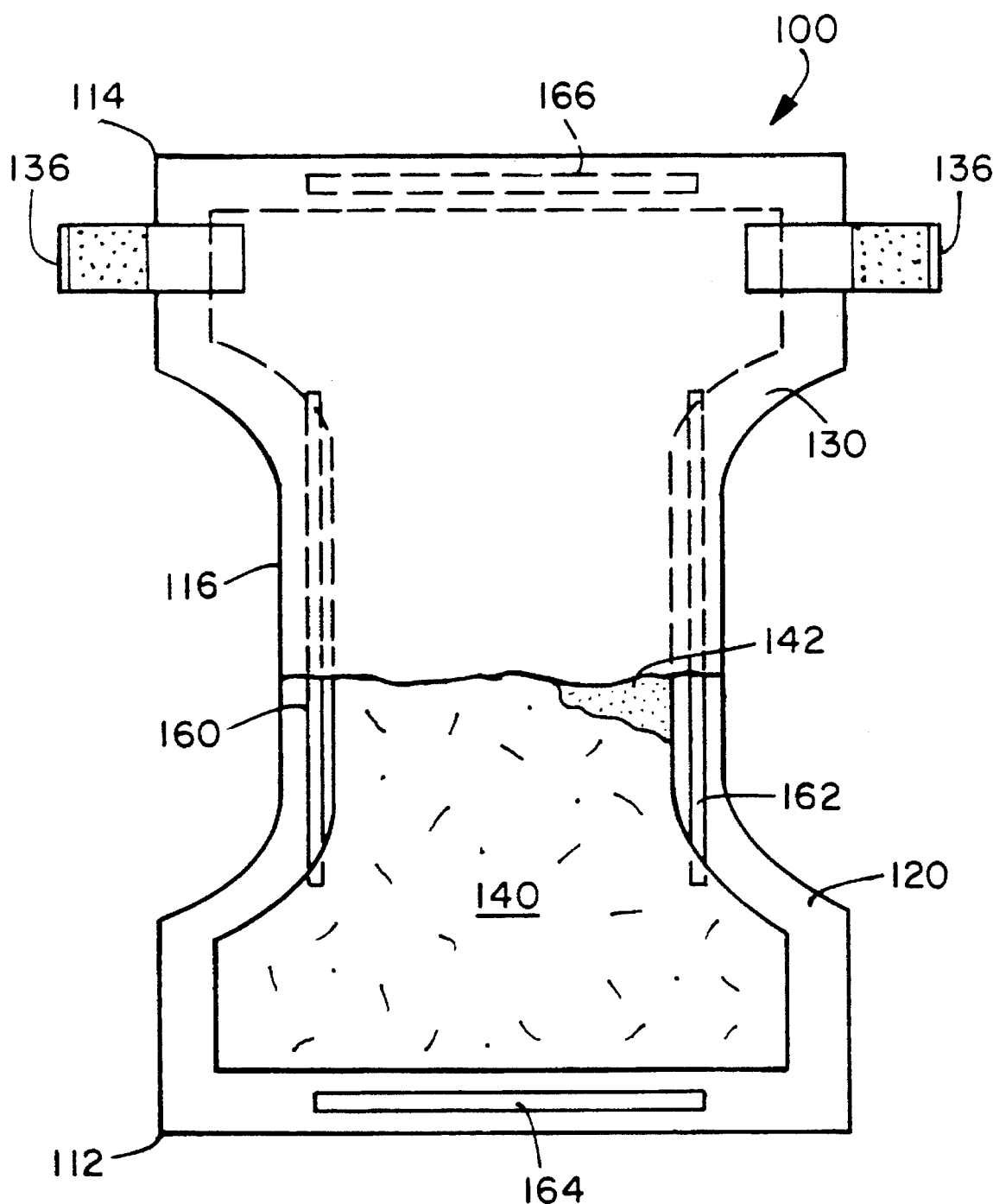
FIG. 6 is a partial plan view of an absorbent diaper type article made according to a preferred embodiment of the present invention. Portions of some layers of the articles have been removed to expose the interior of the article.

Turning to FIG. 6, a disposable diaper-type article 100 made according to a preferred embodiment of the present invention is shown. The diaper 100 includes a front waistband panel section 112, a rear waistband panel section 114, and an intermediate section 116 which interconnects the front and rear waistband sections. The diaper comprises a substantially liquid impermeable outer cover layer 120, a liquid permeable liner layer 130, and an absorbent body 140 located between the outer cover layer and the liner layer. Fastening means, such as adhesive tapes 136 are employed to secure the diaper 100 on a wearer. The liner 130 and outer cover 120 are bonded to each other and to absorbent body 140 with lines and patterns of adhesive, such as a hot-melt, pressure-sensitive adhesive. Elastic members 160, 162, 164 and 166 can be configured about the edges of the diaper for a close fit about the wearer.

The outer cover layer 120 can be composed of the fabric of the present invention bonded to a polymer film comprising polyethylene, polypropylene or the like.

The liner layer 130 and absorbent body 140 can also be made of the nonwoven fabric of the present invention. It is desirable that both the liner layer 130 and the absorbent body 140 be hydrophilic so that aqueous fluids such as urine pass through the liner and are absorbed and retained by the absorbent body. Although not shown in FIG. 6, the disposable diaper 100 may include additional fluid handling layers such as a surge management material layer, a transfer layer or a distribution layer. These layers may be separate layers or may be integral with the liner layer 120 or the absorbent body 140.

Although the absorbent article 100 shown in FIG. 6 is a disposable diaper, it should be understood that the nonwoven fabric of the present invention may be used to make a variety of absorbent articles such as those identified above.

The following Examples 1–4 are designed to illustrate particular embodiments of the present invention and to teach one of ordinary skill in the art in the manner of carrying out the present invention. Comparative Examples 1–4 are designed to illustrate the advantages of the present invention. It should be understood by those skilled in the art that the parameters of the present invention will vary somewhat from those provided in the following Examples depending on the particular processing equipment that is used and the ambient conditions.

COMPARATIVE EXAMPLE 1

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 50 openings per inch in the machine direction. The core composition was 100% by weight PP-3445 polypropylene from Exxon Chemical Company of Houston, Tex., and the sheath composition was 100% by weight PD-9355 random copolymer of ethylene and propylene from Exxon. The random copolymer comprised 3% by weight ethylene. The melt temperature in the spin pack was 430° F. and the spinhole throughput was 0.7 GHM. The quench air flow rate was 22 scfm and the quench air temperature was 55° F. The aspirator teed temperature was 55° F. and the manifold pressure was 5 psi. The resulting nonwoven web was thermal point bonded at a bond temperature of 260° F. The bond pattern had regularly spaced bond areas with 270 bond points per square inch and a total bond area of about 18%. The filaments had a denier of 3.4.

EXAMPLE 1

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 50 openings per inch in the machine direction. The core composition was 100% by weight PP-3445 polypropylene from Exxon Chemical Company of Houston, Tex., and the sheath composition was 80% by weight PD-9355 random copolymer of ethylene and propylene (3% ethylene) from Exxon and 20% by weight Duraflex® DP-8510 copolymer of butene-1 and ethylene from Shell Chemical Company of Houston, Tex. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting nonwoven web was thermal point bonded at a bond temperature of 260° F. The bond pattern had regularly spaced bond areas with 270 bond points per square inch and a total bond area of about 18%. The strands had a denier of 3.4.

EXAMPLE 2

A nonwoven fabric was made according to the process described in Example 1 except that the sheath component was 70% by weight PD-9355 random copolymer of ethylene and propylene from Exxon and 30% by weight of Duraflex® DP-8510 butene-1/ethylene copolymer from Shell Chemical Company.

Fabric samples from Comparative Example 1 and Examples 1 and 2 were tested to determine their physical properties. The data from these tests are shown in Tables 1 and 2. The numbers not enclosed by parentheses represent actual data and the numbers in parentheses represent data normalized to 1.1 osy.

The grab tensile (peak energy, peak load, and peak elongation) was measured according to ASTM D 1682 in both the machine direction (MD) and the cross direction (CD). In Table 1, MD/CD average means the sum of the MD and CD values divided by 2.

The trapezoid tear is a measurement of the force required to continue or propagate a tear in a nonwoven fabric specimen. The trapezoid tear was measured according to ASTM D 1117-14 except that the tearing load was calculated as the average of the first and highest peaks recorded rather than of the lowest and highest peaks.

The abrasion resistance was measured according to two tests, the first being the Martindale Abrasion test which measures the resistance to the formation of pills and other related surface changes on textile fabrics under light pressure using a Martindale tester. The Martindale Abrasion was measured according to ASTM 04970-89 except that the value obtained was the number of cycles required by the Martindale tester to create a 0.5 inch hole in the fabric sample.

The second abrasion resistance test was the double head rotary platform (Taber) test. The Taber test was performed according to ASTM D-1175 using a 125 gram rubber wheel. The abrasion resistance was measured in cycles to a 0.5 inch hole.

The softness of the fabric samples was determined by measuring the drape stiffness and the cup crush. The drape stiffness was measured according to ASTM D 1388. The cup crush test evaluates fabric stiffness by measuring the peak load required for a 4.5 cm diameter hemispherically shaped foot to crush a 9"×9" piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which might affect the peak load. The peak load is measured while the foot descends at a rate of about 0.25 inches per second (15 inches per minute) utilizing a Model FTD-G-500 load cell (500 gram range) available from the Schaevitz Company, Tennsauken, N.J.

TABLE 1

|  | Comp. Ex. 1 | Ex. 1 | Ex. 2 |
| --- | --- | --- | --- |
| Basis Weight (osy) | 1.07 | 1.08 | 1.16 |
|  | (1.1) | (1.1) | (1.1) |
| Grab Tensile (MD) |  |  |  |
| Peak Energy (in-lb) | 22.3 | 23.1 | 18.9 |
|  | (22.9) | (23.5) | (17.9) |
| Peak Load (lb) | 21.0 | 19.0 | 15.6 |

TABLE 1-continued

|  | Comp. Ex. 1 | Ex. 1 | Ex. 2 |
| --- | --- | --- | --- |
| Peak Elongation (in) | (21.6) 56.8 | (19.4) 70.8 | (14.8) 69.3 |
| Grab Tensile (CD) | | | |
| Peak Energy (in-lb) | 13.3 | 22.2 | 15.4 |
|  | (13.7) | (22.6) | (14.6) |
| Peak Load (lb) | 12.9 | 15.6 | 11.4 |
|  | (13.3) | (15.9) | (10.8) |
| Peak Elongation (in) | 60.0 | 84.6 | 78.7 |
| Grab Tensile | | | |
| MD/CD average | | | |
| Peak Energy (in-lb) | 17.8 | 22.7 | 17.1 |
|  | (18.3) | (23.0) | (16.3) |
| Peak Load (lb) | 16.9 | 17.3 | 13.5 |
|  | (17.4) | (17.6) | (12.8) |
| Trap Tear (lb) | | | |
| MD | 10.9 | 9.0 | 7.2 |
|  | (11.2) | (9.1) | (6.8) |
| CD | 4.0 | 6.6 | 6.5 |
|  | (4.1) | (6.8) | (6.1) |
| MD/CD average | 7.4 | 7.8 | 6.8 |
|  | (7.6) | (7.9) | (6.5) |

TABLE 2

|  | Comp. Ex. 1 | Ex. 1 | Ex. 2 |
| --- | --- | --- | --- |
| Martindale Abrasion Cycles to 0.5 in hole | 734 | 735 | 462 |
| Taber Abrasion 1-CS10 Wheel | 80 | 82 | 46 |
| Drape Stiffness (in) | | | |
| MD | 3.46 | 2.79 | 2.83 |
| CD | 2.54 | 2.37 | 2.16 |
| Cup Crush | | | |
| Peak Load(g) | 114 | 100 | 93 |
| Total Energy (g/mm) | 2030 | 1878 | 1696 |

As can be seen from the data in Tables 1 and 2, the addition of the butene polymer substantially enhanced the softness of the nonwoven bicomponent fabric as indicated by the drop in the drape stiffness and the cup crush, but did not reduce the strength properties of the fabric to undesirable levels. In Example 1, wherein the butene polymer was present in the amount of 20% by weight of the sheath, the strength properties were increased and the fabric was softened. At the higher loading of 30% by weight butene polymer in the sheath in Example 2, the fabric was softened further but some of the fabric's strength was lost.

COMPARATIVE EXAMPLE 2

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 50 openings per inch in the machine direction. The core composition was 100% by weight PP-3445 polypropylene from Exxon Chemical Company of Houston, Tex., and the sheath composition was 100% by weight PD-9355 random copolymer of ethylene and propylene from Exxon. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting strands of the web had a denier of 3.0. The web was thermal point bonded to opposite sides of a 0.4 osy basis weight middle meltblown nonwoven fabric web comprising 100% by weight PD-3495G polypropylene available from Exxon. The composite was made in accordance with U.S. Pat. No. 4,041,203. The resulting composite was thermal point bonded at a bond temperature of 280° F. The bond pattern had regularly spaced bond areas with 270 bond points per square inch and a total bond area of about 18%.

EXAMPLE 3

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 50 openings per inch in the machine direction. The core composition was 100% by weight PP-3445 polypropylene from Exxon Chemical Company of Houston, Tex., and the sheath composition was 85% by weight PD-9355 random copolymer of ethylene and propylene from Exxon and 15% by weight Duraflex® DP-8510 copolymer of butene-1 and ethylene from Shell Chemical Company of Houston, Tex. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting strands of the web had a denier of 3.0. The first web was thermal point bonded to opposite sides of a 0.4 osy basis weight middle meltblown nonwoven fabric web comprising 100% by weight PP-3495G polypropylene available from Exxon. The composite was made in accordance with U.S. Pat. No. 4,041,203. The resulting composite was thermal point bonded at a bond temperature of 275° F. The bond pattern had regularly spaced bond areas with 270 bond points per square inch and a total bond area of about 18%.

Fabric samples from Comparative Example 2 and Example 3 were tested to determine their physical properties using the same test methods used to test the samples of fabric from the foregoing examples. The data from these tests are shown in Tables 3 and 4. Again, the numbers not enclosed by parentheses represent actual data and the numbers in parentheses represent data normalized to a basis weight of 1.5 osy.

As can be seen from Tables 3 and 4, the fabric sample from Example 3, wherein the sheath component of the bicomponent spunbond material contained 15% by weight butene polymer, was softer than the fabric sample from Comparative Example 2 and had strength properties that were not substantially different than the fabric sample from Comparative Example 2. The greater softness of the sample from Example 3 is most evident from by the cup crush test results. The results of the strength property tests were mixed. The MD and CD peak elongation, the CD peak energy, and the trap tear showed an increase in strength due to the addition of the butene polymer but the remaining grab tensile data showed a decrease in strength. The abrasion resistance was decreased somewhat by the addition of the butene polymer.

TABLE 3

|  | Comp. Ex. 2 | Ex. 3 |
| --- | --- | --- |
| Basis Weight (osy) | 1.54 | 1.50 |
|  | (1.50) | (1.50) |
| Grab Tensile (MD) |  |  |
| Peak Energy (in-lb) | 14.4 | 12.9 |
|  | (14.0) | (12.9) |
| Peak Load (lb) | 17.8 | 14.3 |
|  | (17.3) | (14.3) |
| Peak Elongation (in) | 39.7 | 43.2 |
| Grab Tensile (CD) |  |  |
| Peak Energy (in-lb) | 15.0 | 15.8 |
|  | (14.6) | (15.8) |
| Peak Load (lb) | 12.2 | 9.5 |
|  | (11.9) | (9.5) |
| Peak Elongation (in) | 67.9 | 92.0 |
| Grab Tensile |  |  |
| MD/CD average |  |  |
| Peak Energy (in-lb) | 14.7 | 14.3 |
|  | (14.3) | (14.3) |
| Peak Load (lb) | 15.0 | 11.9 |
|  | (14.6) | (11.9) |
| Trap Tear (lb) |  |  |
| MD | 7.1 | 7.6 |
|  | (6.9) | (7.6) |
| CD | 4.1 | 5.0 |
|  | (4.0) | (5.0) |
| MD/CD average | 5.6 | 6.3 |
|  | (5.5) | (6.3) |

TABLE 4

|  | Comp. Ex. 2 | Ex. 3 |
| --- | --- | --- |
| Martindale Abrasion Cycles to 0.5 in hole | 1213 | 1071 |
| Taber Abrasion 1-CS10 Wheel | 59 | 31 |
| Drape Stiffness (in) |  |  |
| MD | 3.57 | 3.82 |
| CD | 2.52 | 2.26 |
| Cup Crush |  |  |
| Peak Load(g) | 233 | 157 |
| Total Energy (g/mm) | 4229 | 2901 |

COMPARATIVE EXAMPLE 3

A first nonwoven fabric web comprising continuous single component filaments was made with the process illustrated in FIG. 1 and described above except that only one polymer was used. The spinhole geometry was 0.6 mm D with an L/D ratio of 4:1 and the spinneret had 50 openings per inch in the machine direction. The filament composition was 100% by weight PD-9355 random copolymer of ethylene and propylene from Exxon. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting strands of the web had a denier of 3.0. The web was thermal point bonded to opposite sides of a 0.4 osy basis weight middle meltblown nonwoven fabric web comprising 100% by weight PD-3495G polypropylene available from Exxon. The composite was made in accordance with U.S. Pat. No. 4,041,203. The resulting composite was thermal point bonded at a bond temperature of 285° F. The bond pattern had regularly spaced bond areas with 270 bond points per square inch and a total bond area of about 18%.

EXAMPLE 4

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 50 openings per inch in the machine direction. The core composition was 100% by weight PP-3445 polypropylene from Exxon Chemical Company of Houston, Tex., and the sheath composition was 50% by weight PP-3445 polypropylene from Exxon, 30% by weight PD-9355 random copolymer of ethylene and propylene from Exxon, and 20% by weight Duraflex® DP-8510 copolymer of butene-1 and ethylene from Shell Chemical Company of Houston, Tex. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting strands of the web had a denier of 3.0. The first web was thermal point bonded to opposite sides of a 0.4 osy basis weight middle meltblown nonwoven fabric web comprising 80% by weight LH452 random copolymer of propylene and ethylene available from Himont Incorporated of New Castle County, Del., and 20% by weight Duraflex® DP-8911 copolymer of butene-1 and ethylene from Shell Chemical Company. The random copolymer of propylene and ethylene contained 3% by weight of ethylene and the butene polymer contained 94% by weight 1-butene and 6% by weight ethylene. The composite was made in accordance with U.S. Pat. No. 4,041,203. The resulting composite was thermal point bonded at a bond temperature of 275° F. The bond pattern had regularly spaced bond areas with 270 bond points per square inch and a total bond area of about 18%.

Fabric samples from Comparative Example 3 and Example 4 were tested to determine their physical properties using the same test methods used to test the samples of fabric from the foregoing examples. The data from these tests are shown in Tables 5 and 6. Again, the numbers not enclosed by parentheses represent actual data and the numbers in parentheses represent data normalized to a basis weight of 1.6 osy.

As can be seen from Tables 5 and 6, the fabric sample from Example 4, wherein the sheath component of the bicomponent spunbond material and the meltblown layer contained 20% by weight butene polymer, was softer than the fabric sample from Comparative Example 3. The greater softness of the sample from Example 4 is evident from the drape stiffness and cup crush test results. The results of the strength property tests were mixed, but overall, the grab tensile data showed a decrease in strength while the trap tear data showed an increase in strength. The abrasion resistance was decreased by the addition of the butene polymer.

TABLE 5

|  | Comp. Ex. 3 | Ex. 4 |
| --- | --- | --- |
| Basis Weight (osy) | 1.47 | 1.75 |
|  | (1.60) | (1.60) |
| Grab Tensile (MD) |  |  |
| Peak Energy (in-lb) | 16.7 | 15.2 |

TABLE 5-continued

|  | Comp. Ex. 3 | Ex. 4 |
| --- | --- | --- |
|  | (18.2) | (13.9) |
| Peak Load (lb) | 11.6 | 12.3 |
|  | (12.6) | (11.2) |
| Peak Elongation (in) | 60 | 57 |
| Grab Tensile (CD) |  |  |
| Peak Energy (in-lb) | 8.9 | 10.7 |
|  | (9.7) | (9.8) |
| Peak Load (lb) | 7.3 | 6.1 |
|  | (7.9) | (5.6) |
| Peak Elongation (in) | 59 | 85 |
| Grab Tensile |  |  |
| MD/CD average |  |  |
| Peak Energy (in-lb) | 12.8 | 13.0 |
|  | (14.0) | (11.8) |
| Peak Load (lb) | 9.4 | 9.2 |
|  | (10.3) | (8.4) |
| Trap Tear (lb) |  |  |
| MD | 5.7 | 7.6 |
|  | (6.2) | (6.9) |
| CD | 4.6 | 4.7 |
|  | (5.1) | (4.3) |
| MD/CD average | 5.2 | 6.2 |
|  | (5.6) | (5.6) |

TABLE 6

|  | Comp. Ex. 3 | Ex. 4 |
| --- | --- | --- |
| Martindale Abrasion Cycles to 0.5 in hole | 427 | 184 |
| Drape Stiffness (in) |  |  |
| MD | 3.79 | 3.33 |
| CD | 2.66 | 2.17 |
| Cup Crush |  |  |
| Peak Load(g) | 243 | 171 |
| Total Energy (g/mm) | 4494 | 3313 |

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

We claim:

1. A multi-component polymeric spunbond strand including first and second polymeric components and having a cross-section, a length, and a peripheral surface wherein:
   the first and second polymeric components are arranged in substantially distinct zones across the cross-section of the strand and extend continuously along the length of the strand;
   the first polymeric component is a portion of the peripheral surface of the strand continuously along the length of the strand and comprises a blend of a butene polymer and a first polyolefin other than a butene polymer having up to about 10 weight percent of ethylene in polymeric form said butene polymer comprising butene in an amount from about 90 to about 100% by weight of the butene polymer;
   the second polymeric component comprises a second polyolefin having ethylene in an amount less than 10 weight percent.

2. A polymeric strand as in claim 1 wherein the butene polymer is present in the first polymeric component in an amount from about 2 to about 50% by weight of the first component.

3. A polymeric strand as in claim 1 wherein the butene polymer is selected from the group consisting of homopolymer of butene-1 and copolymer of butene-1 and another olefin, the butene-1 being present in the copolymer in an amount from about 90 to about 100% by weight of the copolymer.

4. A polymeric strand as in claim 1 wherein the first polyolefin is present in the first polymeric component in an amount from about 98 to about 50% by weight of the first component, the butene polymer is present in an amount from about 2 to about 50% by weight of the first component, and the butene polymer comprises butene-1 in an amount from about 90 to about 100% by weight of the butene polymer.

5. A polymeric strand as in claim 1 wherein the first polyolefin of the first polymeric component is selected from the group consisting of polypropylene, and copolymers of propylene and ethylene with ethylene being present in an amount from about 1 to about 10% by weight of the copolymer.

6. A polymeric strand as in claim 1 wherein the first polyolefin is present in the first polymeric component in an amount from about 98 to about 50% by weight of the first component, the butene polymer is present in an amount from about 2 to about 50% by weight of the first component, and the butene polymer is selected from the group consisting of homopolymer of butene-1 and copolymer of butene-1 and another olefin, the butene-1 being present in the copolymer in an amount from about 90 to about 100% by weight of the copolymer.

7. A polymeric strand as in claim 1 wherein the second component comprises a second polyolefin including ethylene in an amount up to about 10% by weight of the second component.

8. A polymeric strand as in claim 7 wherein the second polyolefin is selected from the group consisting of polypropylene and copolymers of propylene and ethylene with ethylene being present in an amount from about 1 to about 10% by weight of the copolymer.

9. A polymeric strand as in claim 8 wherein the butene polymer is selected from the group consisting of homopolymer of butene-1 and copolymer of butene-1 and another olefin, the butene-1 being present in the copolymer in an amount from about 90 to about 100% by weight of the copolymer.

10. A polymeric strand as in claim 8 wherein the first polyolefin is present in the first polymeric component in an amount from about 98 to about 50% by weight of the first component, the butene polymer is present in an amount from about 2 to about 50% by weight of the first component, and the butene polymer is selected from the group consisting of homopolymer of butene-1 and copolymer of butene-1 and another olefin, the butene-1 being present in the copolymer in an amount from about 90 to about 100% by weight of the copolymer.

11. A polymeric strand as in claim 1 wherein the first and second components are arranged in a side-by-side configuration.

12. A polymeric strand as in claim 1 wherein the first and second components are arranged in a sheath/core configuration.

13. A polymeric strand as in claim 1 wherein the strands are continuous filaments.

14. A garment comprising a layer of the nonwoven fabric of claim 10.

15. A garment as in claim 14 wherein the garment is one of the group of medical apparel articles.

16. A garment as in claim 14 wherein the garment is a workwear article.

17. A cleaning article comprising a layer of the nonwoven fabric of claim 10.

18. A personal care absorbent article comprising a layer of the nonwoven fabric of claim 10.

19. A personal care absorbent article as in claim 18 wherein the absorbent article is an adult incontinence product.

20. A personal care absorbent article as in claim 18 wherein the absorbent article is an infant diaper.

21. A personal care absorbent article as in claim 18 wherein the absorbent article is a training pant.

22. A personal care absorbent article as in claim 18 wherein the absorbent article is a feminine care absorbent product.

23. A nonwoven fabric comprising the multi-component spunbond strands of claim 1 as a first web.

24. The nonwoven fabric of claim 23 further comprising a second web of extruded polymeric meltblown strands wherein the first and second webs are positioned in laminar surface-to-surface relationship and bonded together to form an integrated fabric.

25. The nonwoven fabric of claim 24 further comprising a third spunbond web of extruded polymeric strands bonded to said second web on the side opposite said first web.

26. A nonwoven fabric comprising the multi-component strands of claim 10 as a first web.

27. The nonwoven fabric of claim 26 further comprising a second web of extruded polymeric meltblown stands wherein the first and second webs are positioned in laminar surface-to-surface relationship and bonded together to form an integrated fabric.

28. The nonwoven fabric of claim 27 further comprising a third spunbond web of extruded polymeric strands bonded to said second web on the side opposite said first web.

* * * * *

UNITED STATES PATENT AND TRADEMARK OFFICE
CERTIFICATION OF CORRECTION

PATENT NO. : 5,512,358

DATED : April 30, 1996

INVENTOR(S): Shawver et al.

It is certified that errors appears in the above-identified patent and that said Letters Patent is hereby corrected as shown below:

Column 10, line 35, "skilled the" should read --skilled in the--;

Column 11, line 35, "teed" should read --feed--;

Column 20, line 12, "stands" should read --strands--;

Abstract, line 47, "or" should read --of--;

Signed and Sealed this

Seventeenth Day of December, 1996

Attest:

BRUCE LEHMAN

*Attesting Officer*     *Commissioner of Patents and Trademarks*